United States Patent [19]

Stern et al.

[11] 4,094,646

[45] June 13, 1978

[54] RAPID METHOD OF ASSAYING COLLAGEN IN MEAT AND MEAT PRODUCTS

[75] Inventors: David L. Stern, Baltimore; Daniel B. Samchuck, Towson, both of Md.

[73] Assignee: The Baltimore Spice Company, Baltimore, Md.

[21] Appl. No.: 802,600

[22] Filed: Jun. 2, 1977

[51] Int. Cl.$^2$ .................. G01N 21/24; G01N 33/16
[52] U.S. Cl. ........................... 23/230 R; 23/230 B
[58] Field of Search ..................... 23/230 B, 230 R

[56] References Cited

U.S. PATENT DOCUMENTS

| | | | |
|---|---|---|---|
| 3,936,271 | 2/1976 | Statter | 23/230 B |
| 3,980,434 | 9/1976 | Mertz | 23/230 B |
| 4,009,390 | 2/1977 | Satterlee | 23/230 B |

OTHER PUBLICATIONS

R. J. Elliott et al., Anal. Biochem, 70(1), pp. 268–273 (1976).
Chemical Abstracts, 66: 75054s (1967).

*Primary Examiner*—Sidney Marantz
*Attorney, Agent, or Firm*—Lawrence I. Field

[57] ABSTRACT

A rapid method for assaying collagen in meat and meat products. A sample of the material being tested is subjected to a controlled, incomplete hydrolysis of the amino acids with an acidified solution of stannous chloride in such a way that all of the tryptophan is completely destroyed but only a portion of the hydroxyproline is hydrolyzed. The percent collagen is correlated with the percent hydroxyproline, colorimetrically determined.

3 Claims, No Drawings

RAPID METHOD OF ASSAYING COLLAGEN IN MEAT AND MEAT PRODUCTS

This invention relates to a rapid, reliable and reproducible method for assaying collagen in meat. More particularly, it relates to an improvement in the methods of assaying collagen presently practiced in the United States and in Europe.

In one commonly practiced method of assaying collagen in meat samples, the procedure involves defatting the meat, freeze drying the sample prior to hydrolyzing the amino acids in the sample, then hydrolyzing the amino acids followed by separating the same by chromatography, elution of the hydroxyproline and finally a colorimetric measurement of the hydroxyproline. The method is time consuming and is too long and complicated to be useful as a production tool even in a moderate size laboratory in a plant processing meat and meat products.

Laboratory methods for determining hydroxyproline are described in the literature, e.g. by Neuman and Logan, J. Biological Chemistry 184 299 (1950) and Prockop and Udenfriend, Analytical Biochemistry, 1 228 (1960), but these are not practiced in commercial operations.

A somewhat simpler method is known to be in use in Europe in which the collagen content of meat and sausage products is assayed by a determination of the hydroxyproline therein. In this method a weighed amount of finely chopped meat product is wrapped loosely in tin foil and the resulting packet is placed in a glass flask into which an acid solution of tin chloride is introduced. The solution is heated and maintained at temperature for 16 to 36 hours, long enough to completely hydrolyze all of the amino acids. The resulting solution is washed into a measuring flask, diluted to the extent desired and then the hydroxyproline content is read by means of a colorimeter.

The present invention is directed to the aforesaid method and is based on a modification of the conditions under which the hydrolysis step is performed, so that a less than complete hydrolysis is effected, along with complete destruction of the tryptophan in the sample, whereby less than about one hour and one-half is required for an accurate assay of the collagen content of a meat or meat product.

The invention will be better understood from the description of a preferred embodiment of the invention, which is intended to illustrate and not to limit the invention.

EXAMPLE

Five (5) grams of meat product are wrapped loosely in a piece of tin foil approximately two inches square. The resulting packet is dropped into a 250 ml flask. Thirty (30) ml of a tin chloride, hydrochloric acid solution prepared by slurrying 17.5 grams of $SnCl_2$ in 140 ml of water and 350 ml of HCl (37%), is added.

The resulting mixture is boiled for thirty-three (33) minutes in a flask equipped with an air condenser and distilling column. The end of the distilling column is immersed into 900 ml of water to which one gram of NaOH has been added. A few drops of phenolphthalein are added as an indicator. At the end of 33 minutes the flask is removed, distillate is wahsed down from inside of the air condensor and the flask. The contents are permitted to cool for a few minutes and are then transferred to a 500 ml volumetric flask. Water is added to the 500 ml mark.

The solution is then filtered through a 15 CM filter paper. Two clean glass tubes are obtained and seven and one-half (7.5) ml of chloramine buffer is added to each tube. The chloramine buffer is prepared as follows:

A first buffer solution (pH 6.0) is made up by dissolving the following in water:
25 grams citric acid
17 grams NaOH
6 ml $CH_3COOH$ (concentrated)
60 grams sodium acetate·$3H_2O$ Water is added to make 500 ml and then (5) drops of toluol are added as a preservative.

250 ml of the above (pH 6.0 buffer) is mixed with 122 ml of n-propanol and 50 ml of water to form a second propanol buffer solution.

The final chloramine buffer added to the glass tubes is prepared by adding 1.41 grams of chloramine T to 200 ml water and 90 ml of the propanol buffer solution.

In the first glass tube one half (½) ml of water is placed and to this seven and one half (7.5) ml of chloramine buffer solution, which will serve as a blank. The tube is stoppered, swirled by hand to insure thorough mixing and is permitted to stand for 10 minutes.

In the second glass test tube, one half (½) ml of the filtrate from the meat sample is placed with the seven and one-half (7.5) ml of chloramine buffer solution. The tube is stoppered, swirled by hand to insure thorough mixing and is also permitted to stand for 10 minutes alongside the blank glass cell containing the ½ ml of water.

At the end of 10 minutes two and (2.5) ml of a freshly prepared color reagent is added to both glass tubes. This reagent is made by suspending 15 grams of 4-dimethylaminobenzaldehyde in 62 ml of n-propanol after which 26 ml of 60% perchloric acid ($HClO_4$) are slowly added and the resulting solution is permitted to cool.

The color reagent is added to the glass tube containing the filtrate and to the blank tube containing water. Then the tubes are stoppered loosely and placed in a heating block at 61° C for fifteen (15) minutes. Then both glass tubes are stoppered tightly and cooled under cold tap water. At the end of four (4) minutes, the blank is removed from the cooling process, inserted into the colorimeter, and standardized to 100%. At the end of 5 minutes cooling, the glass tube containing the ½ ml of filtrate from the meat sample is removed from the cooling process, inserted into the meter and read.

The following table gives the conversion factors for one such meter. For collagen percents greater than 5%, a dilution can be made by adding ¼ ml of filtrate instead of ½ ml and the final results on the conversion table can be multiplied by the appropriate factor of 2.

| COLLAGEN CONVERSION CHART | | | |
| --- | --- | --- | --- |
| METER READING | % COLLAGEN | METER READING | % COLLAGEN |
| .915 | .188 | .280 | 3.108 |
| .880 | .282 | .269 | 3.204 |
| .847 | .376 | .259 | 3.290 |
| .815 | .471 | .249 | 3.387 |
| .785 | .565 | .240 | 3.484 |
| .756 | .659 | .231 | 3.581 |
| .727 | .753 | .222 | 3.667 |
| .700 | .847 | .214 | 3.763 |
| .674 | .941 | .206 | 3.880 |
| .648 | 1.035 | .199 | 3.956 |
| .624 | 1.129 | .187 | 4.043 |
| .600 | 1.226 | .184 | 4.139 |
| .578 | 1.323 | .177 | 4.237 |

-continued
COLLAGEN CONVERSION CHART

| METER READING | % COLLAGEN | METER READING | % COLLAGEN |
|---|---|---|---|
| .556 | 1.419 | .170 | 4.334 |
| .536 | 1.505 | .164 | 4.419 |
| .515 | 1.602 | .158 | 4.516 |
| .496 | 1.699 | .152 | 4.613 |
| .478 | 1.785 | .146 | 4.710 |
| .460 | 1.882 | .141 | 4.796 |
| .442 | 1.978 | .135 | 4.892 |
| .426 | 2.075 | .130 | 4.989 |
| .410 | 2.161 | .125 | 5.086 |
| .394 | 2.258 | .121 | 5.172 |
| .880 | 2.355 | .115 | 5.269 |
| .365 | 2.452 | .112 | 5.366 |
| .352 | 2.538 | .108 | 5.462 |
| .339 | 2.634 | .104 | 5.548 |
| .326 | 2.731 | .099 | 5.645 |
| .314 | 2.828 | .096 | 5.742 |
| .302 | 2.914 | .092 | 5.839 |
| .291 | 3.011 | | |

The accelerated procedure of the present invention is predicated on total destruction of the tryptophan and incomplete hydrolysis of the hydroxyproline to a known extent,. Thirty-three minutes of boiling gives 42% hydrolysis of the hydroxyproline, less than 20 minutes of boiling fails to insure complete destruction of the tryptophan, more than one hour of boiling does not appear to add to the reliability. Obviously the colorimeter read out must conform to the precent hydrolysis, the table above being for one such hydrolysis. In the method none of the amino acids other than hydroxyproline and tryptophan give a reaction with the color producing agent described above. Hence the tyrptophan must be eliminated to permit reading of the hydroxyproline.

We claim:

1. A rapid method for assaying collagen in a simple of meat or meat products comprising hydrolyzing the amino acids in said sample under conditions such that all of the tryptophan therein is destroyed and only a portion of the hydroxyproline therein is hydrolyzed and then determining the percent collagen by colorimetrically reading the present hydroxyproline which has been hydrolyzed and extracted.

2. The method of claim 1 wherein the hydrolysis is effected in an acidified solution of tin chloride ($SnCl_2$).

3. The method of claim 2 wherein the hydrolysis is effected by boiling said sample for between 20 minutes and 90 minutes in said acidified solution of stannous chloride.

* * * * *